United States Patent [19]
Goble et al.

[11] Patent Number: 5,931,840
[45] Date of Patent: *Aug. 3, 1999

[54] BONE FIXATOR FOR A LIGAMENT ANCHOR SYSTEM

[75] Inventors: E. Marlowe Goble, Logan; Thomas Wade Fallin, Hyde Park, both of Utah; Alan Chervitz, Hopkinton, Mass.; Ramarao Gundlapalli, Logan, Utah

[73] Assignee: Innovasive Corp., Logan, Utah

[*] Notice: This patent is subject to a terminal disclaimer.

[21] Appl. No.: 09/014,739

[22] Filed: Jan. 28, 1998

Related U.S. Application Data

[63] Continuation-in-part of application No. 08/736,554, Oct. 28, 1996, Pat. No. 5,766,750.

[51] Int. Cl.$^6$ .................................................. A61B 17/56
[52] U.S. Cl. .............................................. 606/73; 623/13
[58] Field of Search .............................. 606/73, 72, 104, 606/60, 86; 623/13

[56] References Cited

U.S. PATENT DOCUMENTS

| | | | |
|---|---|---|---|
| 4,870,957 | 10/1989 | Goble et al. | 606/73 |
| 4,997,433 | 3/1991 | Goble et al. | 606/64 |
| 5,152,790 | 10/1992 | Rosenberg et al. | 623/13 |
| 5,766,250 | 6/1998 | Chervitz et al. | 623/13 |

*Primary Examiner*—Guy V. Tucker
*Attorney, Agent, or Firm*—M. Reid Russell

[57] ABSTRACT

A bone fixator for a ligament anchor system and a process its use in an arthroscopic procedure for mounting a ligament graft end in a tunnel formed into a bone. The bone fixator includes threaded footing member for mounting in a bone tunnel, that includes a longitudinal opening formed therethrough, and a ligament carrying member that has a forward of proximal portion for fitting through the threaded footing member longitudinal opening and including a coupling arrangement for securing the ligament carrying member in the threaded footing member. The ligament carrying member further includes as a rear or distal portion that incorporates a ligament mounting section, that, in one embodiment, is an eyelet section to receive a ligament graft fitted therethrough and folded upon itself and in another embodiment is a flat section having a center longitudinal axis wherefrom at least one and preferably a pair of spaced apart pointed posts extend at essentially right angles that include serrations or downwardly sloping teeth formed along at least one side of each post, the post or posts for passing through transverse holes formed in an end of a ligament graft, such as a bone end of a bone tendon ligament graft, with the ligament graft bone end urged onto the mounting plate posts axially mounting it thereto. The ligament carrying member with axially mounted ligament graft are guided in the bone tunnel and into the footing longitudinal opening, with the ligament carrying member to lock therein, completing the ligament graft end mounting in the bone tunnel. With, after the ligament graft is placed under tension and the opposite graft end secured to the tibia cortex, should an adjustment of ligament graft tension be desirable, the footing member is turned appropriately in the bone tunnel.

16 Claims, 14 Drawing Sheets

BONE FIXATOR FOR A LIGAMENT ANCHOR SYSTEM

The application is a continuation in part application of parent application Ser. No. 08/736,554 filed on Oct. 28, 1996 under the same title, now U.S. Pat. No. 5,766,750.

BACKGROUND OF THE INVENTION

1. Field of the Invention

This invention relates to ligament anchor systems and devices for use in surgical procedures for the repair or replacement of a ligament and in particular to a male connector that incorporates a ligament mount or fixator for maintaining a ligament thereto with the male connector for coupling into a female connector seated in a bone tunnel, thereby mounting the ligament in that bone tunnel.

2. Prior Art

In the discipline of arthoscopic surgery, for a ligament replacement procedure, a surgeon will form a tunnel into or through a bone that is to receive a ligament graft maintained therein. For such ligament graft mounting, a ligament graft end has heretofore been connected, as by sewing it to a rear end of a male connector whose forward end is arranged for fitting into a female coupling that has been secured in the ligament tunnel, or the ligament graft has been fitted through and looped over an open fixator end of a male connector that is then fitted into a female coupling. Which male and female connectors to join together, completing the endosteal mounting. An earlier U.S. patent of one of the inventors, U.S. Pat. No. 4,870,957, shows an example of such arrangement that utilizes male and female connectors, with the female connector, like that preferred for the invention, having a threaded outer surface that is for turning into a prepared ligament tunnel. With the male connector, at its end opposite to its ligament mounting end, including, in one embodiment, a spring collet that is for fitting into a longitudinal opening formed through the female connector, exiting the female connector open end. In practice, shown in the '957 patent, with passage of the male member into the opening, the collet lip end will flex outwardly across an edge of the female connector opening proximal end, thereby locking the male to the female member. In another embodiment of the invention, the male member includes an open eyelet distal end that is used for maintaining a ligament graft thereto and employs, as its coupling end, a circular groove formed therein back from a sloping end to fitting into to receive a cross wire seated in the female member that flexes into the groove, prohibiting withdrawal of the male member.

Additional to the above cited earlier U.S. patent of one of the inventors, U.S. Pat. No. 's 4,772,286 , that is also set out in Re. 34,293 ; No. 4,997,433; and 5,129,902, and in a U.S. patent to Jenkins, Jr. No. U.S. Pat. No. 5,571,139 , that also show endosteal mounting arrangements and provide for connecting to a natural or prosthetic ligament, or to sutures, with each such device to function as a mounting. Such couplings of a ligament graft end sutures to a connector, or to a connector element of these prior patents are, however, unlike the fixator arrangement of the present invention in that they do not employ the coupling arrangement of either of the embodiments of the invention. Similarly, U.S. Pat. Nos. 4,744,793; 4,784,126; 5,100,417 and 5,152,790, show bone tunnel mountings that also provide for coupling to a ligament graft end, sutures or the like, but do not employ a ligament graft fixator arrangement that is like that of the present invention.

SUMMARY OF THE INVENTION

It is a principal object of the present invention to provide a bone fixator for a ligament anchor system and procedure for its use for easily and reliably securing a biological or prosthetic ligament graft, or ligament type device, onto a proximal end of male member or component that is for fitting in a seated bone tunnel mounting in a ligament repair or replacement procedure.

Another object of the present invention is to provide a bone fixator for a ligament anchor system that is suitable for use in a procedure for endosteally mounting a ligament in a prepared ligament tunnel in an arthroscopy surgical procedure.

Another object of the present invention is to provide a bone fixator for a ligament anchor system for use in securing a ligament graft, such as a bone end of a bone tendon bone ligament graft, utilizing a male connector member, or utilizing a male connector member that includes an eyelet end to receive a ligament graft fitted therethrough, with the male connector member for fitting into and locking in a female footing that has been mounted in a prepared ligament tunnel.

Another object of the present invention is to provide a bone fixator for a ligament anchor system where, in one embodiment, a locking of a male member thereof in a female member that is seated in a bone tunnel is provided by a spring collet formed on a proximal end of the male member that is fitted through a longitudinal opening in the seated female footing with a lip of the male member spring collet end to flex outwardly so as to pass over the edge of the female footing opening, securely locking to prevent withdrawal of the male member back through the female footing.

Another object of the present invention is to provide a bone fixator for a ligament anchor system that includes, in one embodiment, as a fixator for securing a bone end of a bone tendon bone ligament graft onto a distal portion of the male member, a flat longitudinal distal end section that includes at least one, and preferably a pair of parallel posts, that extend at right angles from the flat surface, are each pointed and each preferably includes at least one side formed with serrations or teeth therealong, the post or posts for passing through the ligament graft bone end, skewering it onto the male member distal end.

Another object of the present invention is to provide another embodiment of a bone fixator for a ligament anchor system that includes, for securing a male connector coupling end in the female member, a contact wire is secured across the female member opening that is to be depressed away from the center of the female member opening by a male connector member end that is passed therein, with that contact wire then flexing back to enter and lock within a groove formed around the male connector member, adjacent to a proximal end of the male connector member.

Still another object of the present invention is to provide a bone fixator for a ligament anchor system that is easily installed in a practice of an arthroscopic surgical procedure to repair or replace a ligament, for example, in a procedure that is practiced on a patient's knee for replacing a cruciate ligament, where a threaded female footing that is open axially therethrough and is arranged to be turned into, to a desired location, in a prepared ligament tunnel, and where a male member, that mounts a ligament graft to a distal end and it arranged to fit a proximal end of that female member, for endosteally mounting an end of that ligament graft therein.

Still another object of the present invention is to provide a process for endosteally mounting a ligament graft end in a prepared ligament tunnel utilizing, as a bone fixator, the threaded footing and male member where the male member proximal end is to fit into the open threaded footing end, and is passed therealong to where a male member coupling locks in the female member, completing an endosteal mounting.

Still another object of the present invention is to provide a process for drilling a tunnel into a bone to a determined depth to receive a ligament graft selected or fabricated to a length to fit in that prepared tunnel.

Still another object of the present invention is to provide a process for drilling a straight tunnel into a bone to receive a female member turned into that tunnel to a desired location as determined by distance markings scribed at intervals along a spade drill that is used in the tunnel formation, which markings are for comparison with an edge of the tunnel end opening.

Still another object of the process of the present invention is to provide for ligament graft initial tensioning by attaching a ligament graft end to the bone cortex surface that is adjacent to the tunnel entrance, as with a staple, or the like, or with the ligament graft already under tension, to provide for fitting a tool to the footing and turning it into or out of the tunnel section to increase or decrease ligament graft tension.

Still another object of the present invention is to provide a bone anchor system, that may be a biodegradable system, and is for mounting a ligament graft, or ligament type device, within a prepared ligament tunnel.

The present invention is in a ligament fixator for a bone fixator for a ligament anchor system and process for its use. Embodiments of the bone fixator of the invention include a threaded cylindrical female footing member that is open longitudinally therethrough and is preferably threaded along its outer surface for turning into the wall of a prepared ligament tunnel section. Which female member, in one embodiment, includes a coupling wire fitted across its longitudinal opening to fit in a groove formed around the male member for coupling the member together; and includes a male member, in another embodiment, having a spring collet forward or proximal end that is for fitting into to pass through the threaded female member longitudinal opening, such that a spring collet outer lip will flex over the edge of the threaded member opening. The spring collet thereby prohibits the male member from being pulled back through the footing.

The male member includes, in one embodiment, as a distal section, a flattened ligament mounting plate wherefrom one, and preferably a pair, of spaced posts, are mounted, each to extend at right angles therefrom. The posts are each pointed at their ends and preferably include, along at least one side of each, and preferably along two opposite sides of each, serrations, teeth, or the like, that are for receiving an end of a ligament graft skewered thereon. Which ligament graft end is preferably a bone end of a bone tendon bone ligament graft, or the like, that preferably will have been drilled appropriately, to fit onto the post or posts, so as to extend axially from the male member distal end. With, in another embodiment, the male member distal end is formed into an eyelet to receive a ligament graft fitted therethrough.

In a practice of the process for securing a ligament graft in a bone, a spade drill is used to form a straight tunnel into one or more bones that the bone anchor system is to be installed in. Such spade drill is preferred, but, or course, other types of drills could be so utilized. The preferred spade drill includes spaced markings scribed at equal intervals therealong that increase in value from a stepped end and are for comparison with an outer end of the formed tunnel for measuring the distance from that tunnel end to a female member seating end. Whereafter, the female member is turned into that tunnel, preferably fully into the tunnel stepped end. For ligament graft installation, the male member, with the ligament graft extending axially therefrom, has its proximal end fitted through the tunnel and into an open end of the threaded footing longitudinal cavity. The male member, in one embodiment, includes a spring collet end that has the cone shaped end that is larger in diameter than that of the treaded footing longitudinal opening and is separated into four equal segments by crossing slots that extend longitudinally into a cylindrical portion thereof. The four segments in the male member end form arcuate segments, that, when passed into the longitudinal opening, will be compressed together and remain so during travel through the threaded footing opening. The spring collet segments are to flex outwardly at the tunnel end with the edge of each segment base undersurface to travel over the edge of a cavity in the threaded footing, prohibiting withdrawal of the male member. With, in another embodiment, the male member includes a circular groove formed therein back from its proximal end and the female member includes a coupling wire secured in and to extend across the longitudinal cavity. The coupling wire to first flex away from the male member end as it is fitted therein, and will then flex back into the male member circular groove, locking the two members together. With the embodiments of the male and female members locked together, the opposite ligament graft end can be placed in tension and connected, as by stapling it to a bone cortex surface that is adjacent to a bone tunnel end, completing the ligament mounting. Which ligament tension can be later adjusted by fitting an appropriate tool through an arthroscopic port to engage the threaded foot and turn it in the tunnel section to increase or decrease ligament tensioning.

The threaded footing that is the female member is turned into the bone tunnel using a turning tool to a selected distance from an open bone tunnel end as determined by markings scribed along the spade drill. A selected length of ligament graft or a ligament type device is secured, as set out above, to the male member, that is then installed in the female member, as set out above. With the ligament graft mounted to extend axially from the male member distal end. The ligament graft can be held by a surgeon operator who, using a driver, that is releasably connected to the male member, or by pulling a line that is connected to extend axially from the male member spring collet end, urges the male member along the tunnel so as to fit it in the distal end into the threaded footing to travel therealong and lock into that threaded foot to endosteally mount the ligament graft in the bone tunnel.

As desired, to release or adjust tension on the ligament graft, a small incision can be made into the knee, to expose an end of the ligament tunnel wherein the threaded footing is turned, allowing access to the male member spring collet end of the footing end. The spring collet end, can be released, as by squeezing the spring collet segments together, allowing back passage through the female member longitudinal opening, releasing the male member, or the ligament tensioning can be adjusted by fitting a turning tool to the threaded footing and turning it appropriately in the ligament tunnel.

BRIEF DESCRIPTION OF THE DRAWINGS

These and other objects and features of the present invention will become more apparent from the following description in which the invention is described in detail in conjunction with the accompanying drawings.

DETAILED DESCRIPTION

Figure 1:
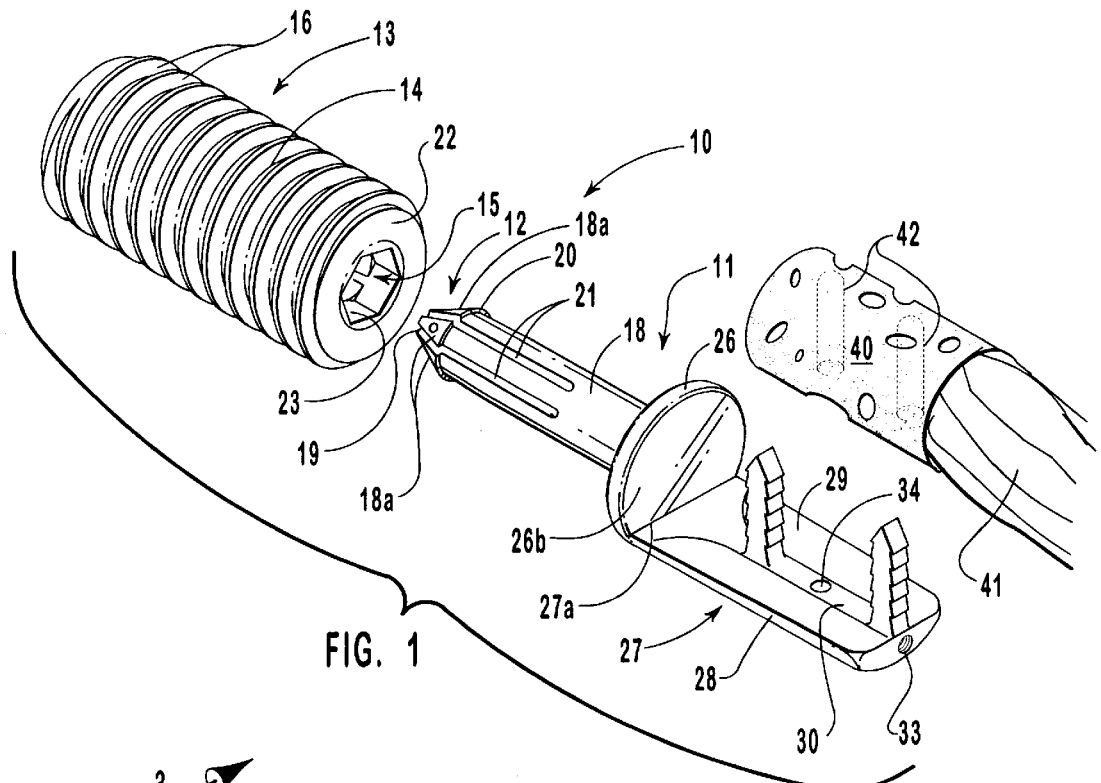
FIG. 1 is a profile perspective view of a first embodiment of the bone fixator or ligament anchor system of the invention showing a threaded footing with a male member proximal end portion cross cut to form a spring collet, and which male member end is aligned for fitting into a longitudinal opening formed through a female member threaded footing, and showing the male member as including a center disk that has a like diameter to that of the footing and wherefrom a distal section extends rearwardly, shown as an arcuate segment, that has a flat surface wherefrom a pair of spaced posts extend at right angles upwardly, and showing a bone of a bone tendon ligament graft positioned for skewering onto the posts.
Figure 2:
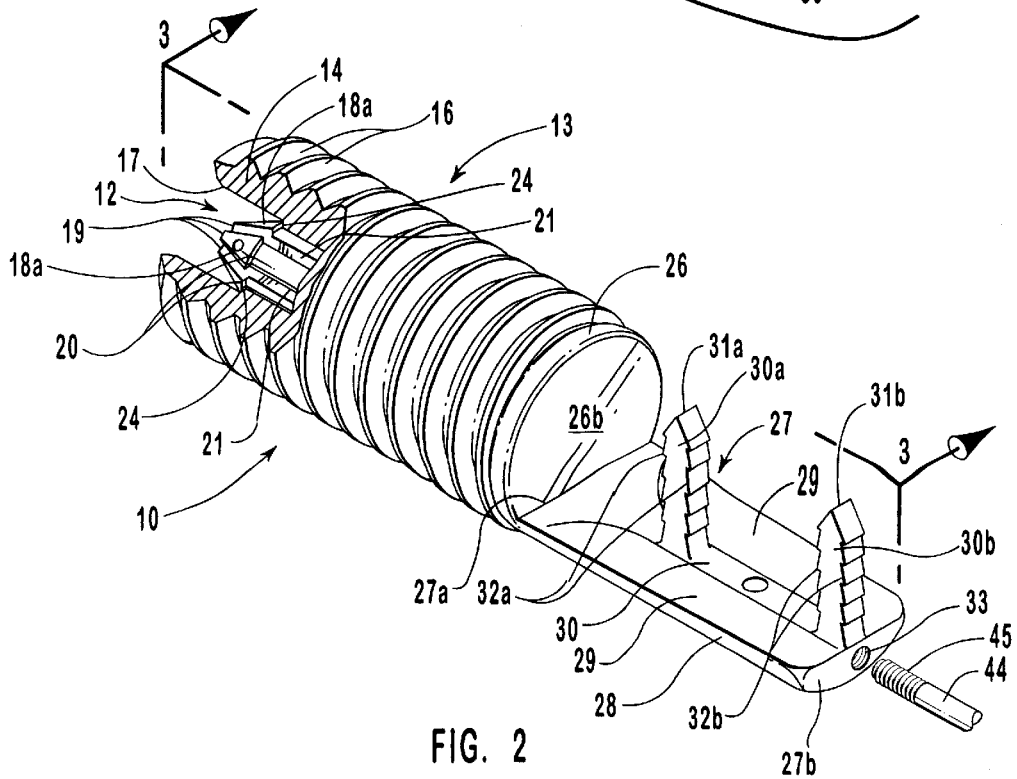
FIG. 2 is a view like that of FIG. 1 only showing the male member as having been fitted into the female threaded footing and showing, through a broken away section, a base edge of the cone shaped spring collet proximal end as having flexed over the edge of a cavity formed in the longitudinal opening of the female member footing proximal end, with a threaded end of a rod type insertion tool aligned for turning into a threaded hole formed in the male member distal end.
Figure 3A:
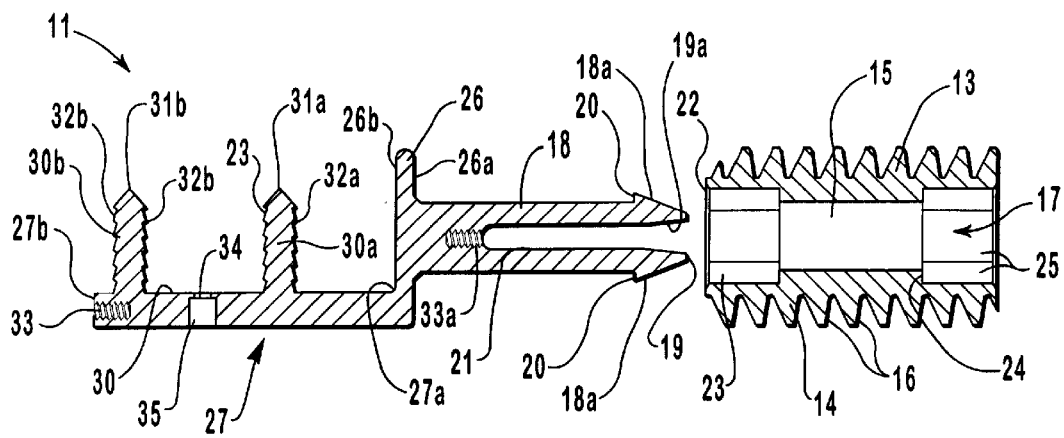
FIG. 3A is a side elevation sectional view taken along the line 3—3 of FIG. 2, showing the male member aligned for fitting into the female member threaded footing longitudinal opening.
Figure 3B:
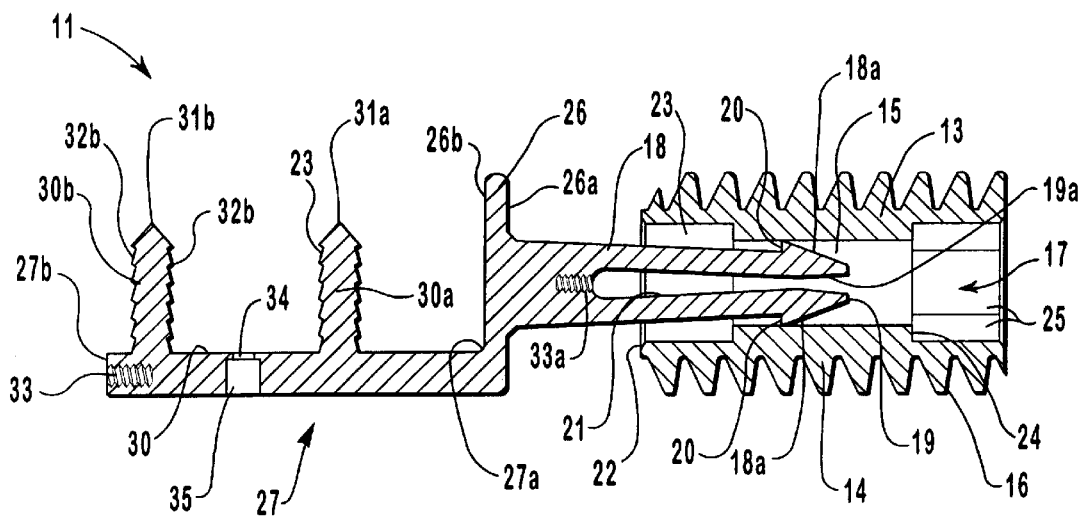
FIG. 3B is a view like that of FIG. 3A showing the spring collet end of the male member as having traveled into the female member threaded footing longitudinal opening.
Figure 3C:
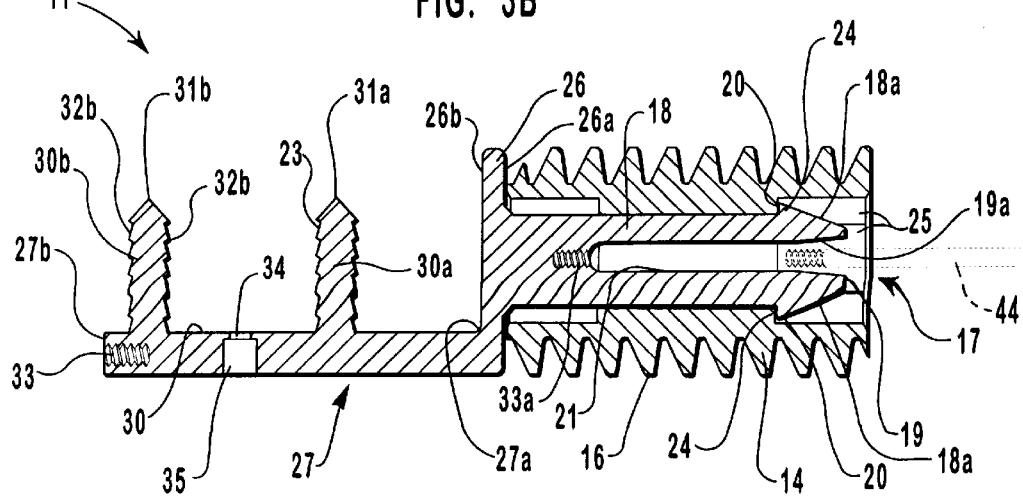
FIG. 3C is a view like that of FIGS. 3A and 3B showing the male member cone shaped spring collet end as having traveled into an outwardly stepped proximal end portion cavity of the female member threaded footing longitudinal opening, with a cone base edge of the spring collet end shown as having flexed over an edge of a step formed in the female member distal end, locking the male member and threaded footing together.

FIG. 1 shows a profile perspective view of a first embodiment of a bone fixator or ligament anchor system 10 of the invention that includes a male member 11. The male member 11 is shown as having a crosscut across a forward or proximal end 12 that is for fitting into a center longitudinal passage 15 in a cylindrical body 14 of a female member threaded footing 13, hereinafter referred to as threaded footing 13. The threaded footing 13 is externally threaded at 16, along its length. Which threads 16 are deep threaded that are for providing a strong purchase when turned in a bone wall of a tunnel 50. Appropriate threads for this use are as shown and described in the cited U.S. Pat. No. 4,870,957 of one of the present inventors. FIG. 2 shows the male member 11 as including a proximal portion 18 that is preferably like that of the '957 patent, and includes the cross-cut end 12 that is shown as a cone 19. The cone 19 is shown cross-cut from its apex longitudinally into the proximal portion 18, forming a spring collet, that is shown in FIGS. 3A and 3B as having been fitted into the center longitudinal passage 15 of the threaded footing 13. The cross-cut end 12, is shown in FIG. 3C, as having passed into an outwardly stepped proximal cavity 17 formed in a proximal end portion of the center longitudinal passage 15, locking therein.

FIG. 2 shows the male member 11 as including the cylindrical forward or proximal portion 18 with the cross-cut end 12 that is preferably a cone shaped tip 19 and is formed into the spring collet by longitudinal slots 21 that are cut from the cone apex through a cone base and into the proximal portion 18. Which slots are at right angles to one another, forming a cross that divides the proximal portion into four like segments 18a. The slots 21 extend longitudinally from the cone 19 apex along the forward or proximal portion 18 to form the proximal segments 18a, as shown best in FIGS. 3A through 3C. The base of cone shaped tip 19 includes an edge 20 that is at approximately a right angle to the proximal portion 18 longitudinal axis. The crossed slots 21 section the cone into the equal proximal segments 18a. So arranged, the cross-cut cone shaped tip 19 functions as the spring collet, with the proximal segments 18a, that are quarter segments, collapsing together, as shown in FIG. 3B, when the cross-cut end 12 is urged into a distal end of the center longitudinal passage 15 of the threaded footing 13.

Figure 4:
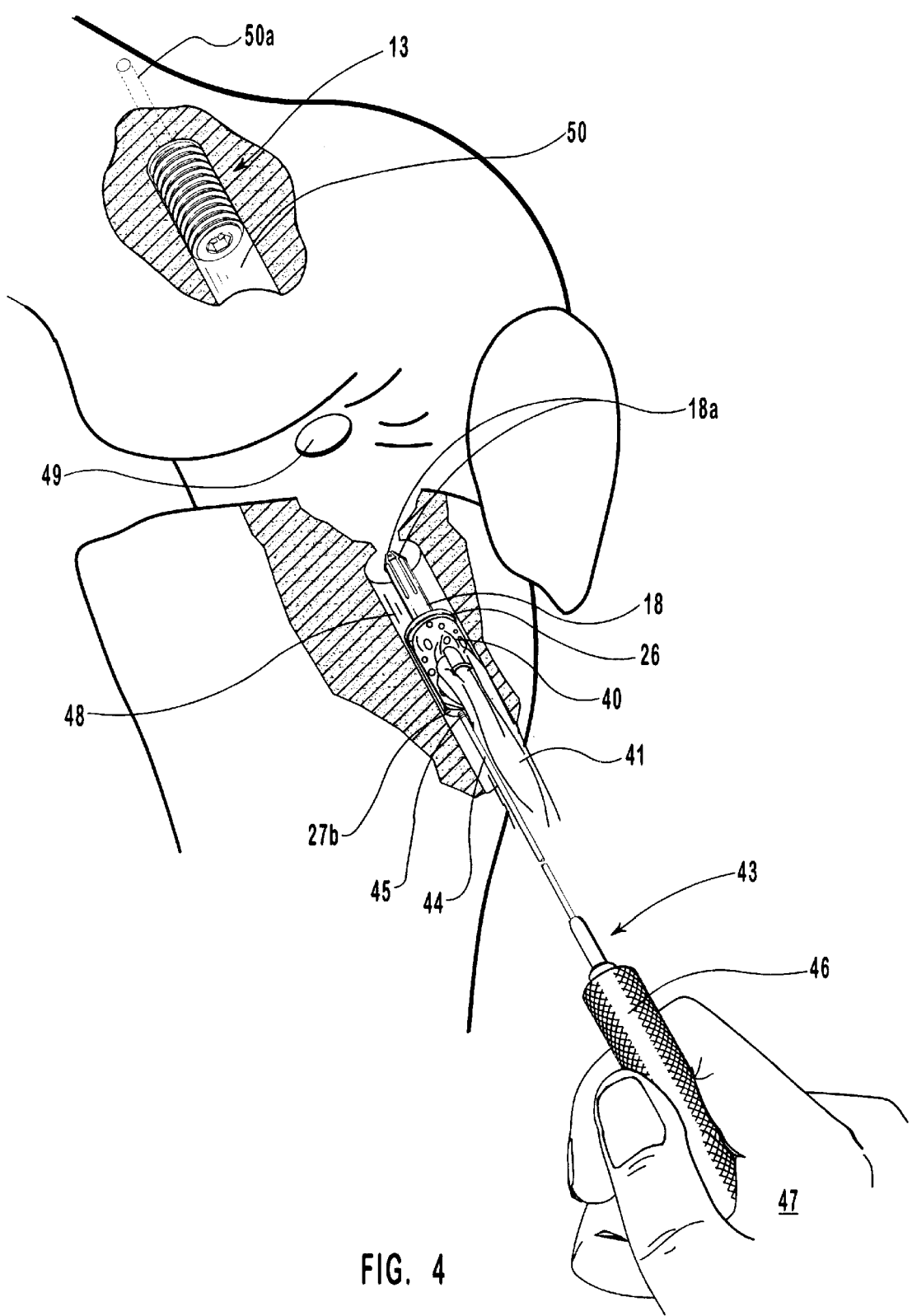
FIG. 4 is a profile perspective view showing a patient's knee, and showing a straight tunnel formed through the proximal tibia, across the interarticular joint and into the distal femur, as a first tunnel section, wherefrom a lesser diameter second tunnel section is shown in broken lines extending therefrom and exiting the bone cortex, with a threaded footing shown as having been turned into the femoral tunnel section and showing a surgeon operator's hand holding a handle end of an insertion tool that includes a straight narrow blade whose end is turned into a threaded hole formed in a male member distal end, with a bone end of a bone tendon ligament graft extending axially from the male member distal end.
Figure 5:
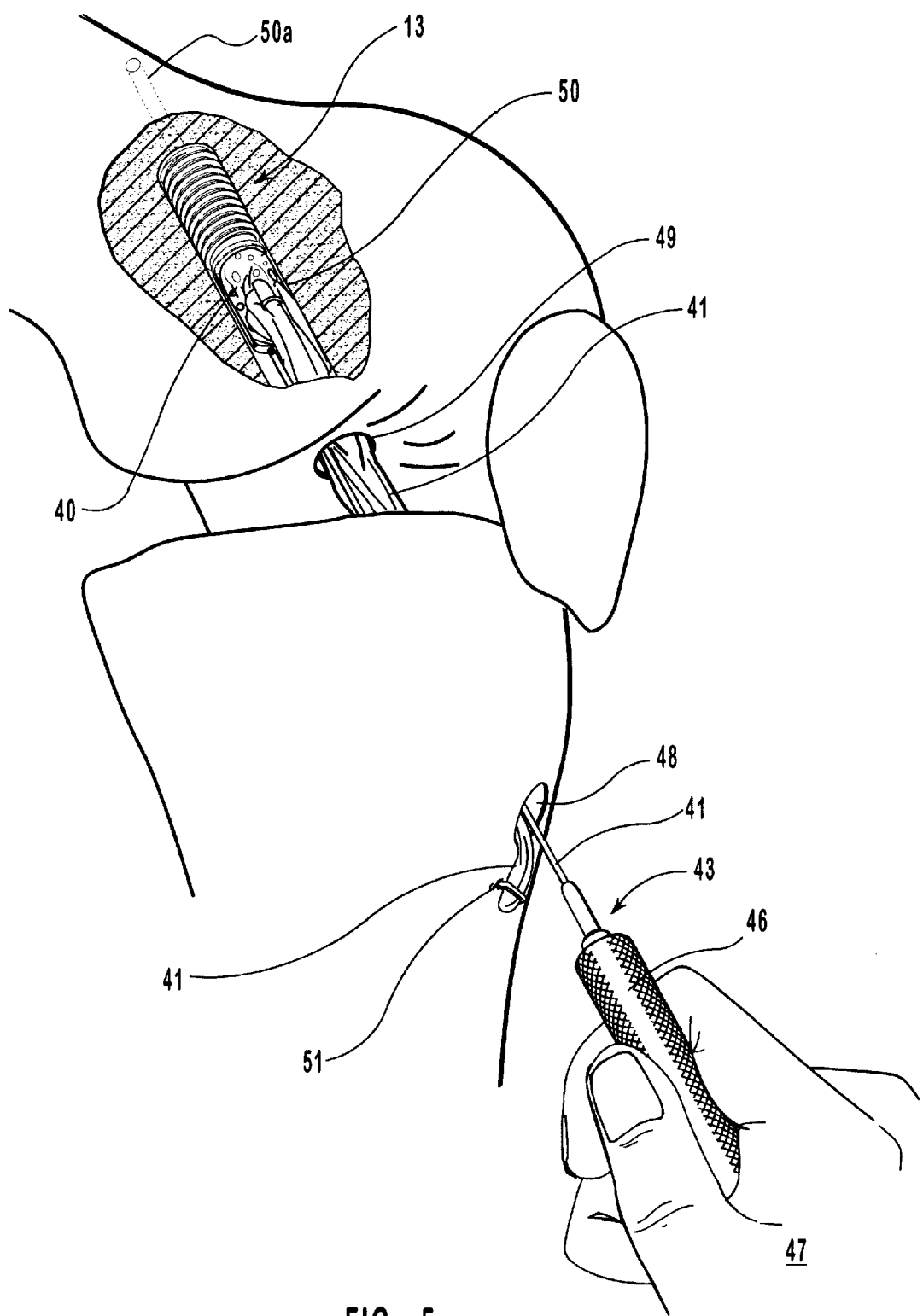
FIG. 5 is a view like that of FIG. 4, only showing the male member as having passed into the femoral tunnel section and into the threaded footing longitudinal opening to lock therein, as shown in FIG. 3C.

The threaded footing 13 proximal end may be formed with a sided opening 25, as shown best in FIG. 1, that preferably has a hexagon cross section, and is to accommodate a turning tool, passed through a femoral second tunnel section 51a, shown in broken lines in FIG. 4, for turning the threaded footing to a proximal end of a first femoral tunnel section 50, as shown in FIGS. 4 and 5. Though, it should be understood, another number of sides greater or less than six sides could be incorporated into sided opening 25, depending upon the configuration of the turning tool, within the scope of this disclosure. Which turning tool such is preferably an Alan wrench that can be fitted through the second tunnel section 50a and into the sided opening 25 after installation for readjusting ligament graft tensioning. Further, as shown best in FIG. 3B, threaded footing 13 includes a distal opening 23 that is also preferably sided to receive an Alan wrench type turning tool, or the like, for turning into the first tunnel section 50, as set out below, which opening is stepped inwardly at the center longitudinal passage 15 with the edge 20 surface of the cone shaped tip 19 proximal segments 18a to contact the step edge to initially flex the proximal segments 18a inwardly to pass into the center longitudinal passage 15. In which passage, the cone shaped tip 19 proximal segments remain flexed together as they pass along that passage 15. At the proximal end of the threaded footing the center longitudinal passage 15, a cavity 17 is formed that is the interior of the sided opening 25 to have a greater diameter than that of the center longitudinal passage 15. The longitudinal passage 15, at its junction to sided opening 25, is thereby stepped outwardly into a flat step 24 that is to receive the surface of base edge 20 of the cone shaped tip 19 proximal segments 18a flexed thereover. Which flexure occurs as the proximal segments 18a flex outwardly when the cone base edge 20 travels beyond the center longitudinal passage 15 proximal end, as shown in FIG. 3C. Preferably, the proximal cavity 17, as set out above, is sided at 25, to receive the turning tool fitted therein, and to later receive the turning tool for adjusting ligament tensioning, as required, though, of course, it need not be sided within the scope of this disclosure.

The male member 11, additional to the described proximal portion 18, and proximal segments 18a includes a disk 26 that is arranged as a male member mid portion. The male member proximal portion is secured to extend axially from a center of a forward face 26a of which disk 26. A ligament mounting plate 27 is secured at an end 27a to extend, at approximately a right angle from a lower section of a distal face 26b of the disk 26 from an edge section thereof. The mounting plate 27 is preferably curved around an undersurface 28 and has an upper face 29 that is essentially flat but may slope slightly between opposite edges into a flat center portion 30, to form a cradle for receiving a bone end of a bone tendon bone ligament graft, as set out below. A pair of spaced aligned posts 30a and 30b are shown extending at approximately right angles upwardly from the flat center portion 30, at spaced interval along its longitudinal center axis, and are each formed to have a rectangular cross section. The posts 30a and 30b are preferably pointed at their top ends 31a and 31b respectively, and are preferably serrated or have downwardly slopping teeth 32a and 32b formed along their opposing sides. The posts 30a and 30b, as shown in FIG. 1, are to fit into transverse holes 42, shown in broken lines, that have been formed across a bone end 40 of a ligament graft 41. So arranged, an operator, not shown, fits the bone end 40 transverse holes 42 onto the post pointed ends 31a and 31b, and pushes on the side of the bone end 40 to pass or skewer the posts 30a and 30b through the transverse holes, to mount the bone end to the upper face, as shown in broken lines. The bone end 40 is thereby axially connected to the male member for fitting, as shown in FIGS. 4 and 5, into a ligament tunnel, as set out and described below. While two spaced posts 30a and 30b are shown, it should be understood that only one such post is required within the scope of this disclosure, and that such post need not have a serrated or toothed side and that more than one such serrated of outwardly sloping toothed side could be so employed within the scope of this disclosure.

For inserting the male member 11, as shown in FIGS. 4 and 5, the mounting plate 27 distal end 27b preferably has a threaded hole 33 formed longitudinally therein that is for receiving a threaded end 45 of a straight shaft 44 of an insertion tool 43, shown in FIGS. 2, 4 and 5. After the bone end 40 is skewered onto the posts 30a and 30b at transverse holes 42, as shown in broken lines in FIG. 1, a pin or tool end, not shown, can be fitted through a hole 35 formed from the curved undersurface 28, through the mounting plate 27, as shown in FIGS. 3A, 3B and 3C. Such pin or tool end, not shown, would travel out of a top end 34 of hole 35 and contact the surface of the bone end 40 for aligning the bone end 40 onto the posts 30a and 30b, or to reset the bone end, the pin or tool end could be used to push the bone end off of the posts 30a and 30b. Such bone end 40 removal would be opposed by the serrated or slopping teeth 32a and 32b.

FIGS. 4 and 5 shown a surgeon/operator's hand 47 holding a handle end 46 of the insertion tool whose threaded end 45 of shaft 44 has been turned into the threaded hole 33 that has been formed into the mounting plate 27 distal end 27b. The threaded member 13 has been fitted, as shown in FIG. 4, through the tibial tunnel section 48 and turned into a femoral tunnel section 50 proximal end, utilizing a sided end of a turning tool, such as an Alan wrench, not shown, that has been fitted into the sided opening 23 formed in the threaded member 13 distal end or can be installed in the cavity 17 and inserted through through an enlarged femoral tunnel section 50a, shown in broken lines. Preferably, the surgeon/operator guides the male member 11 proximal portion 18 through a tibial cortex end of a tibial tunnel section 48 to pass through the interarticular joint and into the distal femoral tunnel end 49 and is fitted into the distal end of the threaded footing 13 center longitudinal passage. Alternatively, as shown in FIGS. 3A, 3B and 3C, a threaded hole 33a is formed in a distal end of slots 21 of male member proximal portion 18 to receive the threaded end 45 of shaft 44 turned therein after the shaft has passed through the second femoral tunnel section 50a and into the first femoral tunnel section 50, and through the tibial tunnel section 48, for use in drawing the male member 11 into the first femoral tunnel section 50. In this arrangement, with the male member proximal portion 18, sections 18a squeezed together reducing the diameter of the passage made by the intersection of the cross-cuts 21 into proximal portion 18 may not be large enough to allow the proximal segments 18a to properly close together, as shown in FIG. 3B. If this is not the case, a hole 19a can be drilled into the proximal end of the cone shaped tip 19 at the intersection of the cross cuts. The hole 19a walls are formed to allow the proximal portion segments 18 to squeeze together, as shown in FIG. 3B, with the shaft 44 fitted therethrough, as shown in FIG. 3B and discussed above. Alternatively, a cable or suture can be used to pull the male member 11 into the threaded footing 13, eliminating a need for forming hole 19a, within the scope of this disclosure.

In practice, the male member proximal portions 18 travel into the threaded footing 13, as shown in FIGS. 3A and 3B, to the seated attitude as shown in FIG. 3C and in FIG. 5. This completes the ligament graft end 40 endosteal mounting in the femoral tunnel section 50. The ligament graft 41 can be placed under tension, with an end thereof that extends from the tibial tunnel section cortex end fixed to the cortex surface as by hammering a staple 51, that straddles the ligament graft end, into the bone cortex, as shown in FIG. 5. The insertion tool 43 can be removed as by turning the threaded end 45 of the shaft 44 out of the threaded hole 33 or threaded hole 33a, or by releasing the suture or cable from the male member proximal end. The insertion tool suture or cable is then pulled out through the tibial tunnel section 48 or the femoral second tunnel section 50a.

Further, after initially setting ligament graft tension, should an adjustment to that tensioning be needed or advisable, a surgeon/operator can refit the turning tool, not shown, through the cortex end of second tunnel section 50a to pass into and engage the footing opening 17 sides 25, for turning the footing into or out of the tunnel section, thereby adjusting ligament graft tension.

Shown best in FIGS. 3A, 3B and 3C, in a passage of the proximal portion 18 proximal segments 18a through the threaded footing 13 center longitudinal passage 15, the sections of the cone shaped tip 19 are initially flexed or collapsed towards one another as they travel through the passage and, at the passage stepped end portion 17, the cone base edge 20 will pass over the step surface 24, prohibiting withdrawal. To release this coupling, a surgeon/operator can form a tunnel, like the second tunnel section 50a, to intersect the femoral tunnel closed end, above the threaded footing proximal end, and can then, utilizing an appropriate tool, collapse together the cone tip 19 and proximal sections 18a together. With the proximal sections 18a collapsed together, the proximal portion 18 is allowed to slide back along the threaded footing 13 longitudinal passage 15, releasing the ligament graft end femoral tunnel section endosteal mounting.

In practice, a threaded footing 13 and male member 11 can be fabricated from a surgically acceptable material including a metal such as titanium, or, within the scope of this disclosure. Further, a resilient plastic material, as shown in the removed section of FIG. 1, such as Delrin™, can also be used for both the threaded footing 13 and the male member 11 to provide, as required, a biodegradable ligament mounting for the bone tendon ligament graft, as shown, or for other ligament graft, within the scope of this disclosure.

Figure 12:
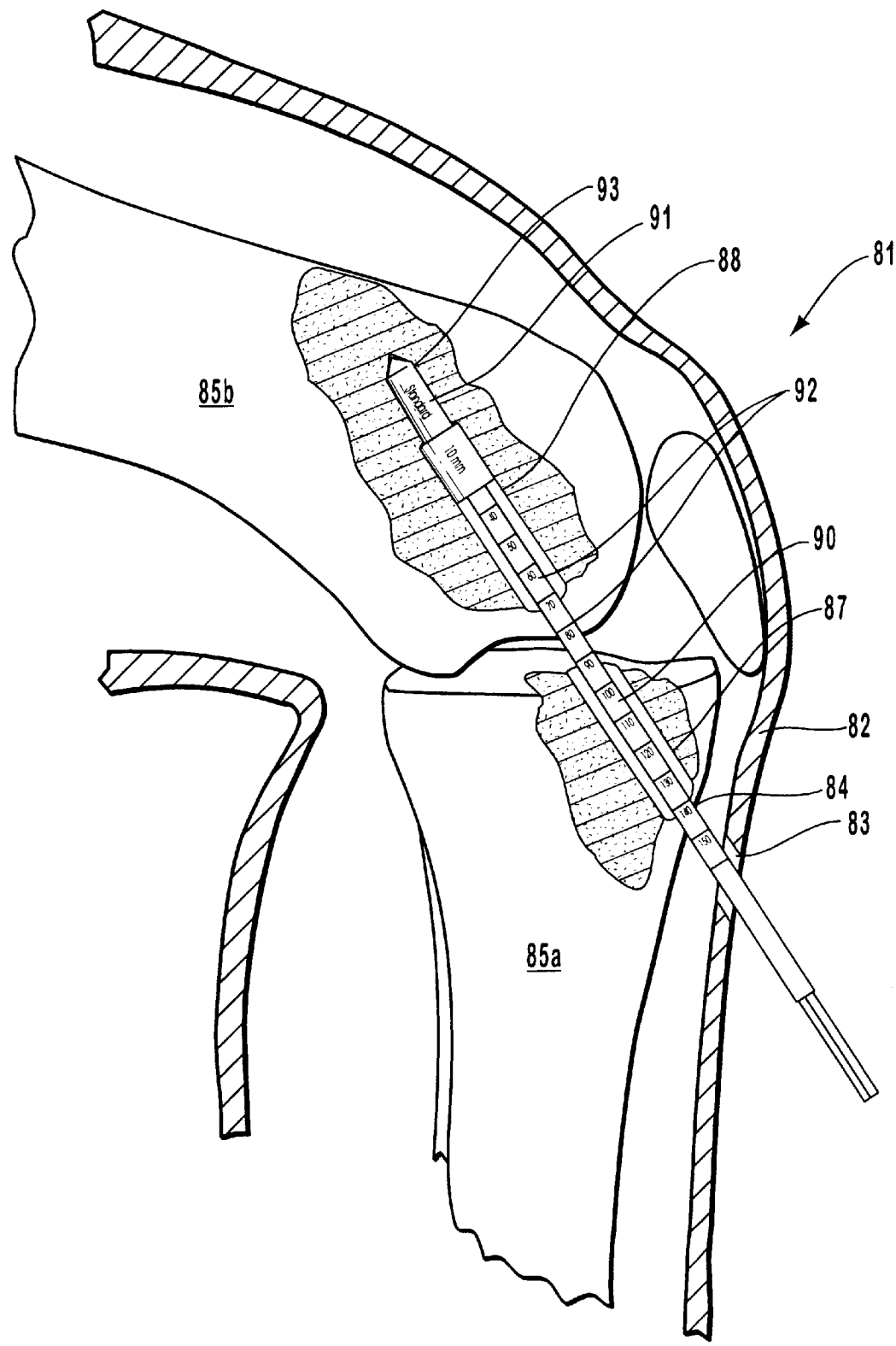
FIG. 12 is a view of the patient's knee like that of FIG. 11 showing a stepped spade drill as having replaced the cannulated spade drill having formed a pilot hole in the tunnel proximal end to receive the female member threaded footing of FIGS. 7A through 7C and 9.
Figure 13:
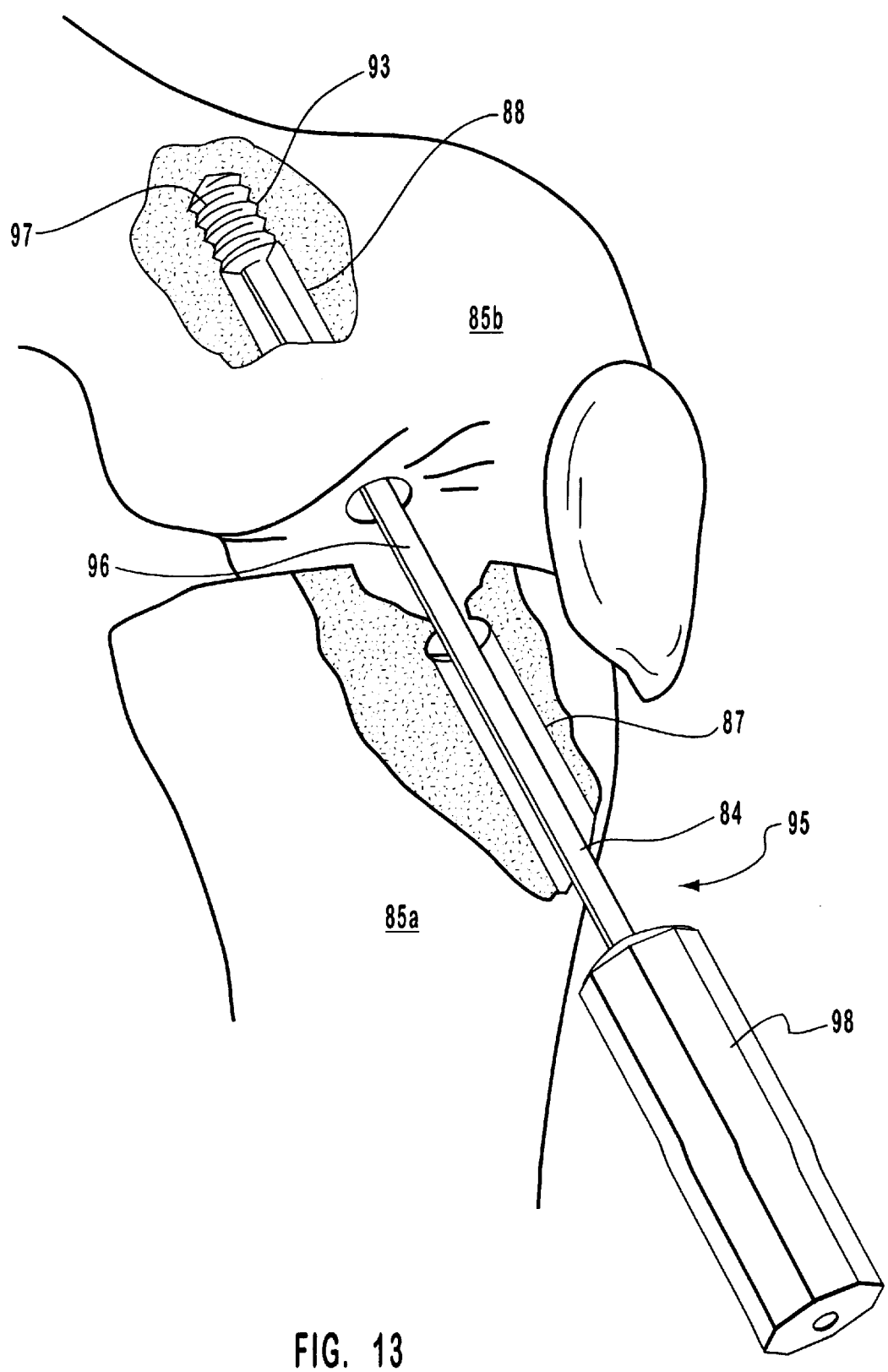
FIG. 13 is a view of the patient's knee like that of FIGS. 11 and 12, showing the stepped spade drill having been removed and replaced by a tap for turning in the tunnel stepped proximal end to form threads to accommodate the female member threaded footing to be turned therein.
Figure 14:
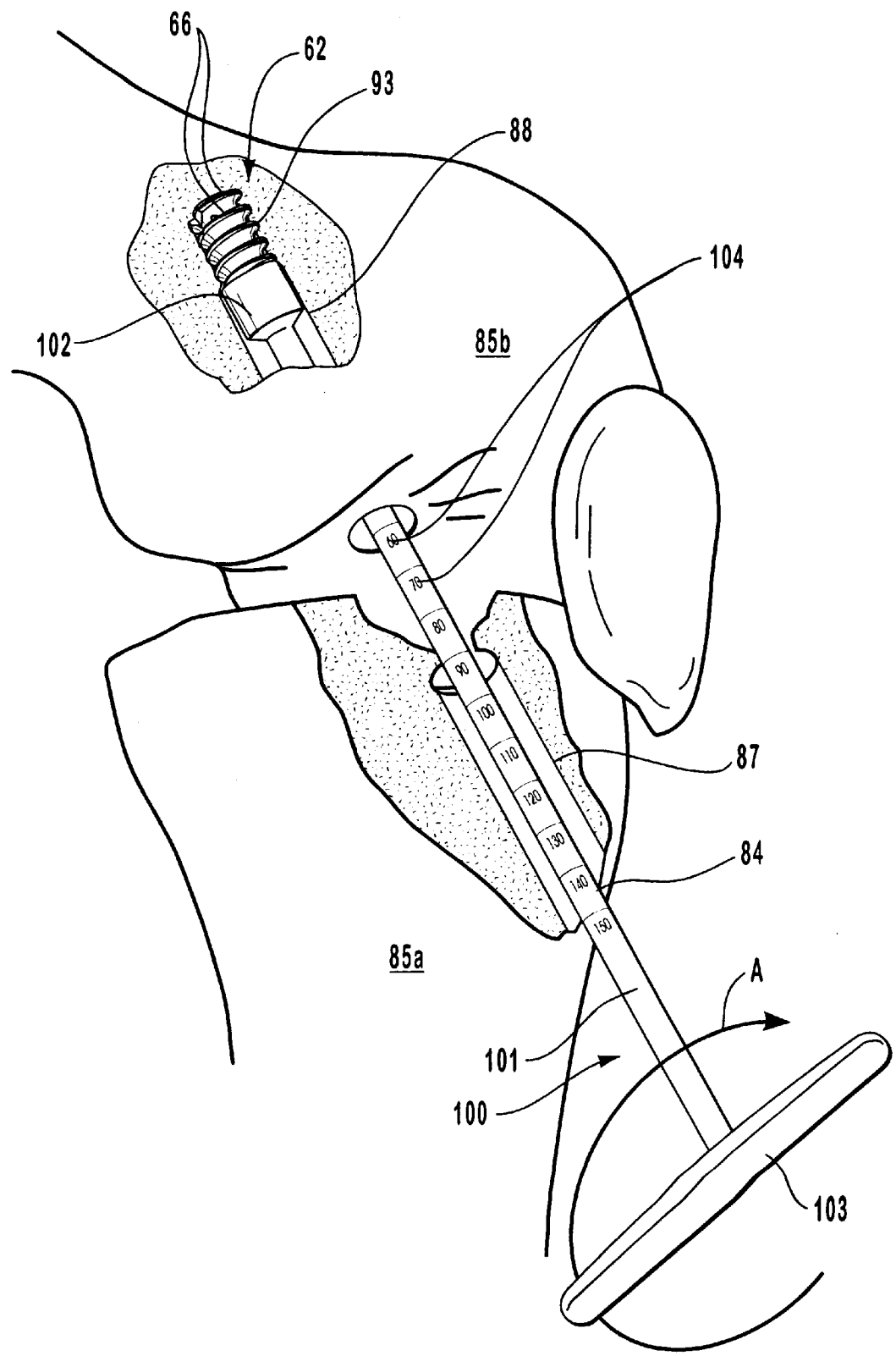
FIG. 14 is a view of the patient's knee like that of FIG. 13 after the tap has been removed and showing a female member threaded footing mounted to the end of a base inserter tool being turned into the tapped hole.
Figure 15:
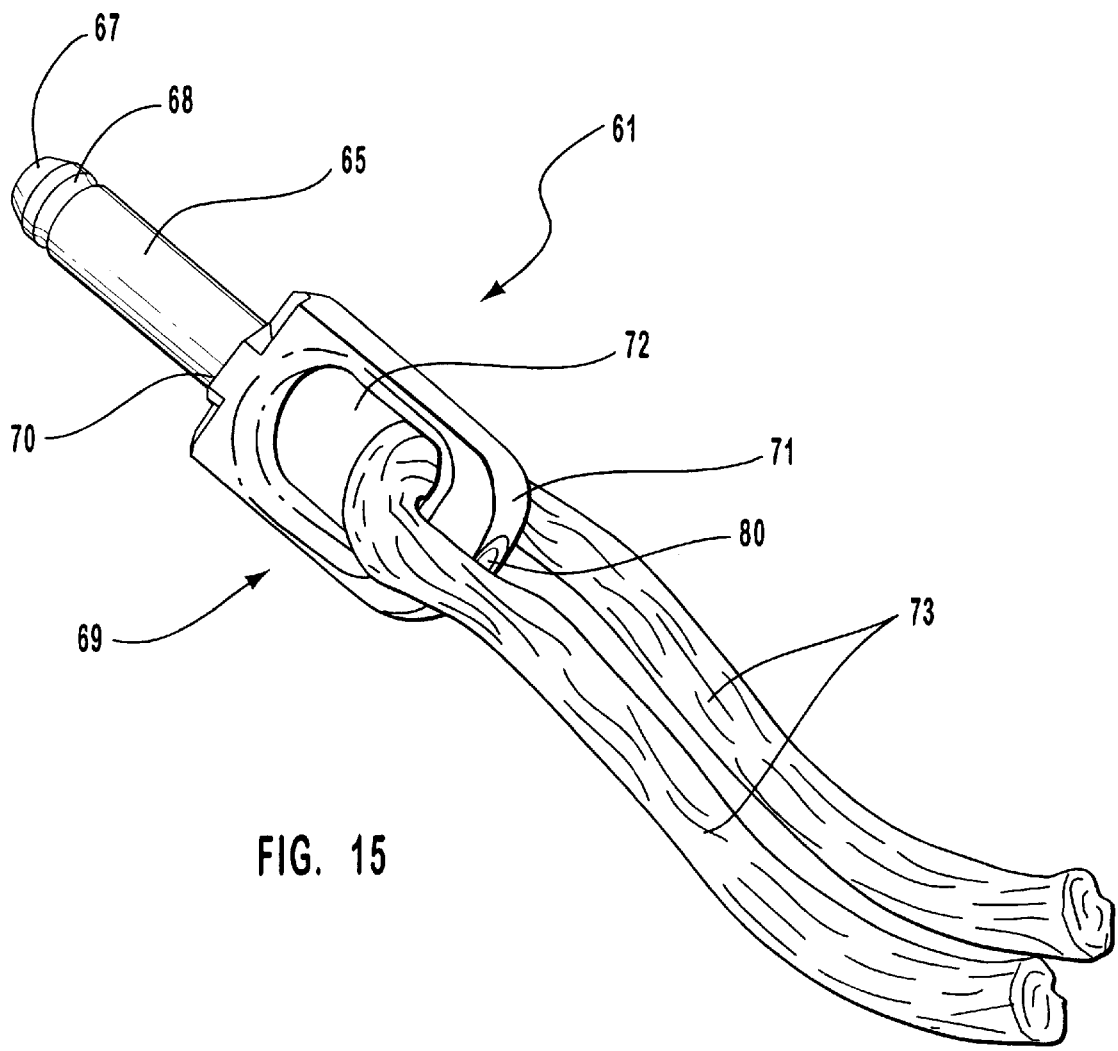
FIG. 15 shows the male member of FIG. 8 having had a ligament graft fitted through its eyelet end.
Figure 16:
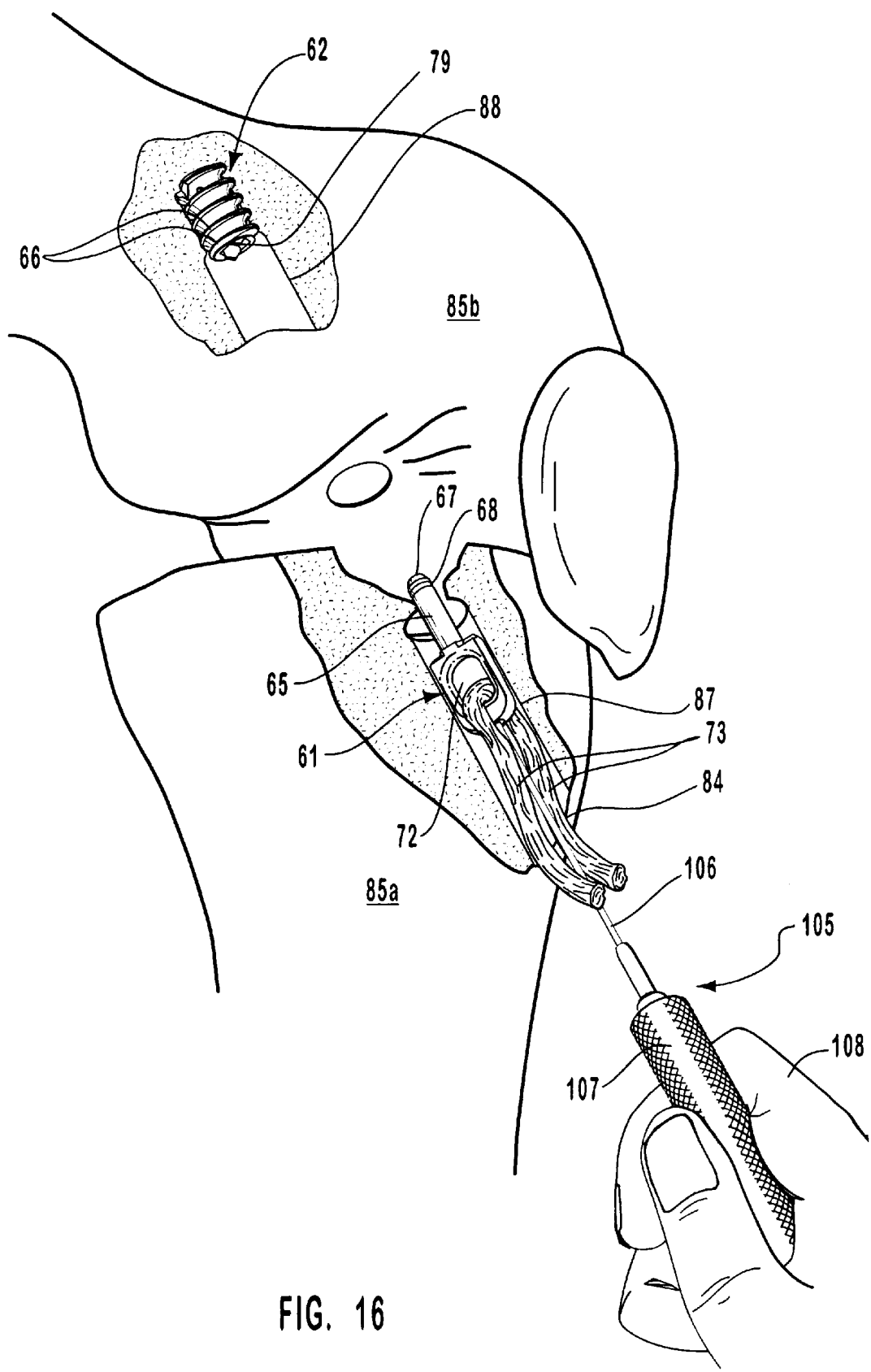
FIG. 16 is a view of the patient's knee like that of FIG. 14 showing the female member threaded footing mounted in the proximal tunnel end and showing the male member of FIG. 15 axially mounted at its distal end onto an end of an insertion tool fitted through the tunnel.
Figure 17:
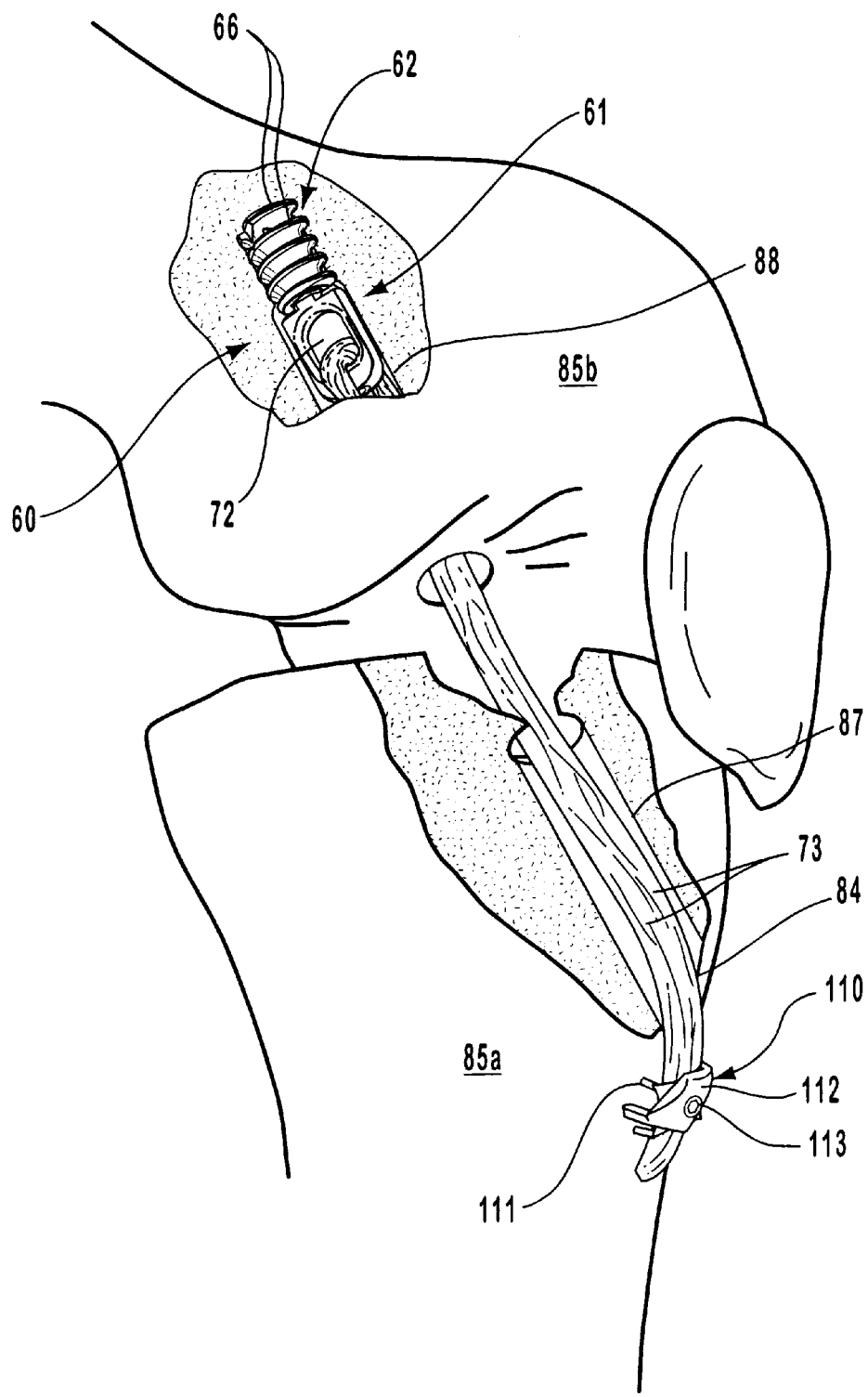
FIG. 17 is a view of the patient's knee like that of FIG. 16 showing the male member as having been installed in the female member threaded footing with the ligament graft pulled tight and secured by a clamp onto the tibia cortex at the tibial tuberosity.

Additional to the bone fixator or ligament anchor system 10 and process or procedure for its use, as set out above, the invention is in an additional embodiment of a bone fixator or ligament anchor system 60, shown in FIGS. 6A through 10, and in a process or procedure for its use for a ligament graft installation in a ligament tunnel, as shown in FIGS. 11 through 17. Shown in the exploded profile perspective view of FIG. 6A the bone fixator or ligament anchor system 60 includes a male member 61 that is for mounting in a female member threaded footing 62, hereinafter referred to as threaded footing. The threaded footing 62 includes a cylindrical body 63 wherein a longitudinal passage or opening 64 is formed for receiving a forward or proximal portion 65 of the male member 61, as shown in FIG. 6B. The threaded footing 62 cylindrical body 63 includes external threads 66 formed along its outer surface that are preferably deep threads that may, as shown by notches the end thread flights, be self tapping to provide a strong purchase when the threaded footing is turned into a bone tunnel wall, as shown in FIGS. 14, 16 and 17.

The male member 61 proximal portion 65 is shown as a cylindrical section that has a tapered forward end 67 and includes a groove 68 formed therearound, adjacent to which tapered forward end. A rear or distal end of the proximal portion 65 connects at a right or normal angle to a forward face 70 of an eyelet member 69 that is shown as a narrow rectangular member that has a rounded rear or distal end 71 and includes a center hole or opening 72 formed therethrough, forming an eyelet. A ligament graft 73 is shown in FIG. 1 for fitting through the opening 72 and is shown threaded therethrough in FIG. 2. Which FIG. 2 shows, in a broken away section of its proximal portion 65, the male member 61 connected into the threaded footing 62 as the ligament anchor system 60. Which connection arrangement is set out hereinbelow with respect of a discussion of FIGS. 7A through 10.

Figure 6A:
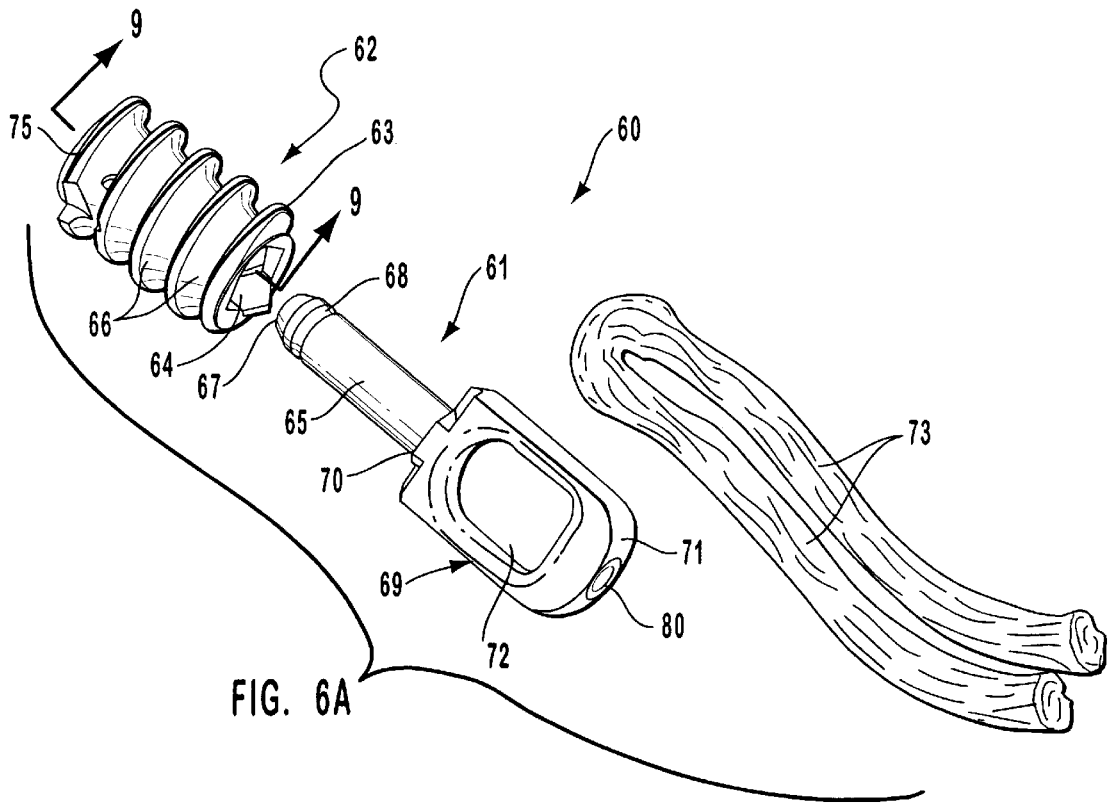
FIG. 6A is an exploded perspective view of another embodiment of a bone fixator or ligament anchor system of the invention showing a male member as including a groove formed around its proximal end section, with the male member aligned for fitting into a longitudinal opening formed in a female member threaded footing and showing the male member distal end as including an eyelet to receive a ligament graft fitted therethrough.
Figure 6B:
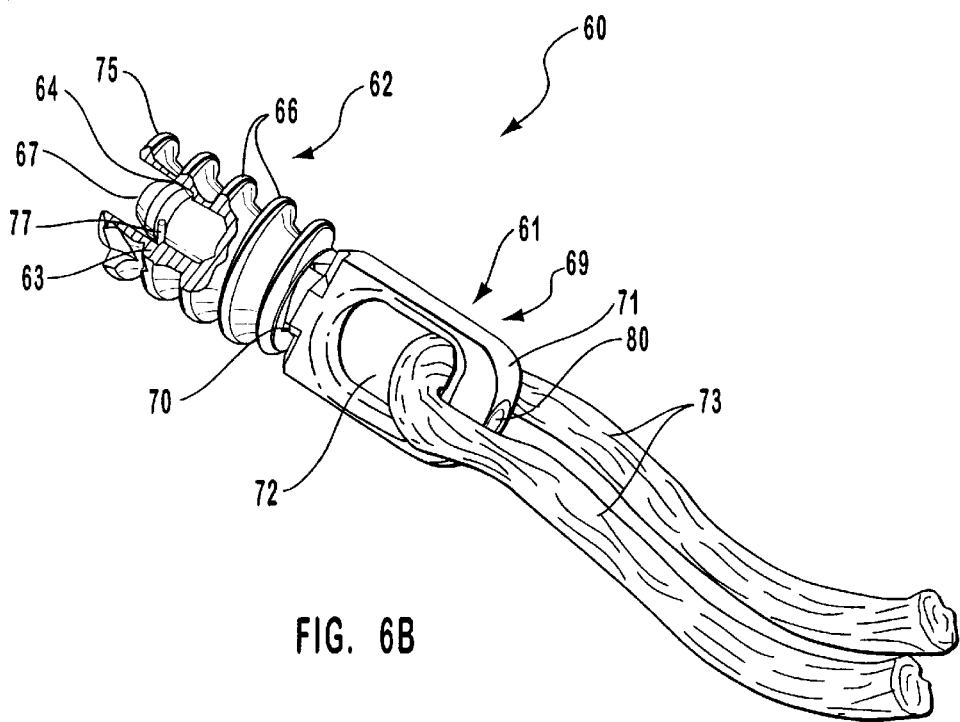
FIG. 6B shows the bone fixator or ligament anchor system of FIG. 6A fitted together.
Figure 7A:
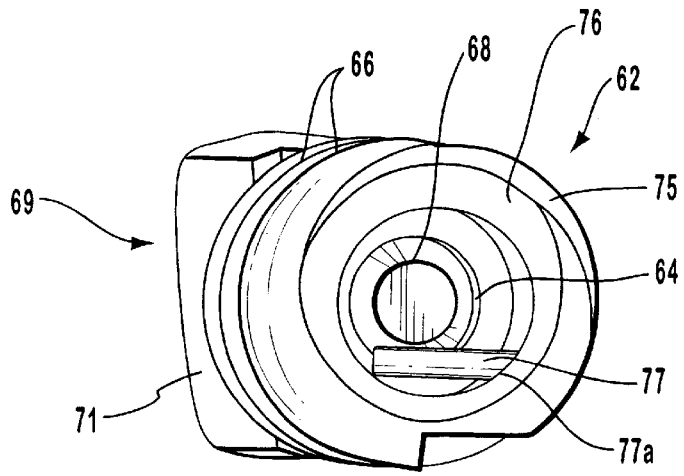
FIG. 7A shows an end plan view of the female member threaded footing taken from its distal end showing a coupling wire secured across a lower section or portion of the threaded member longitudinal passage.
Figure 7B:
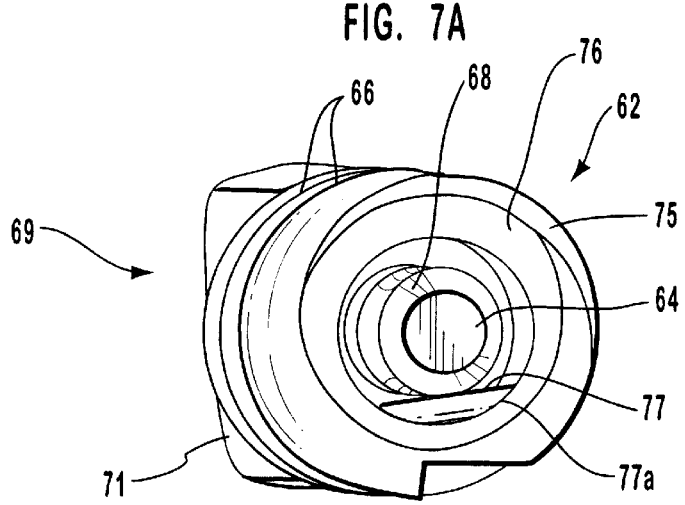
FIG. 7B is a view like that of FIG. 7A showing a sloping proximal end of the male member as having just entered the female member longitudinal passage, deflecting the coupling wire downwardly.
Figure 7C:
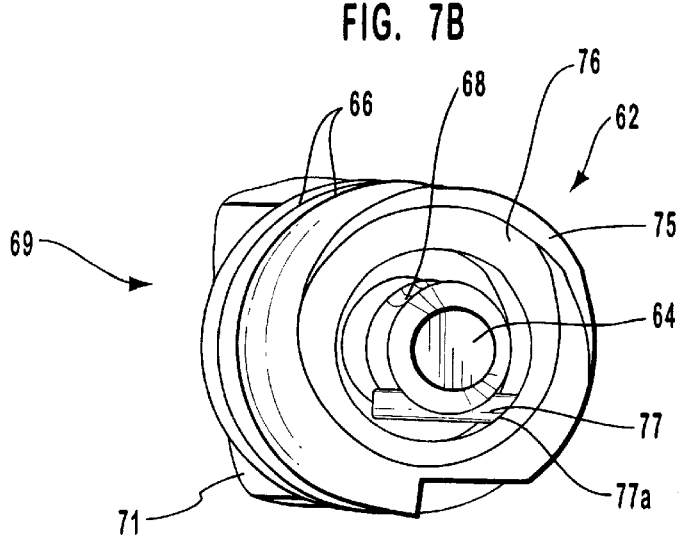
FIG. 7C is a view like that of FIG. 7B showing the male member proximal end as having traveled further into the female member longitudinal passage to where the proximal end section groove aligns with the coupling wire that is shown as have flexed into which groove, locking the male member in the female member.
Figure 10:
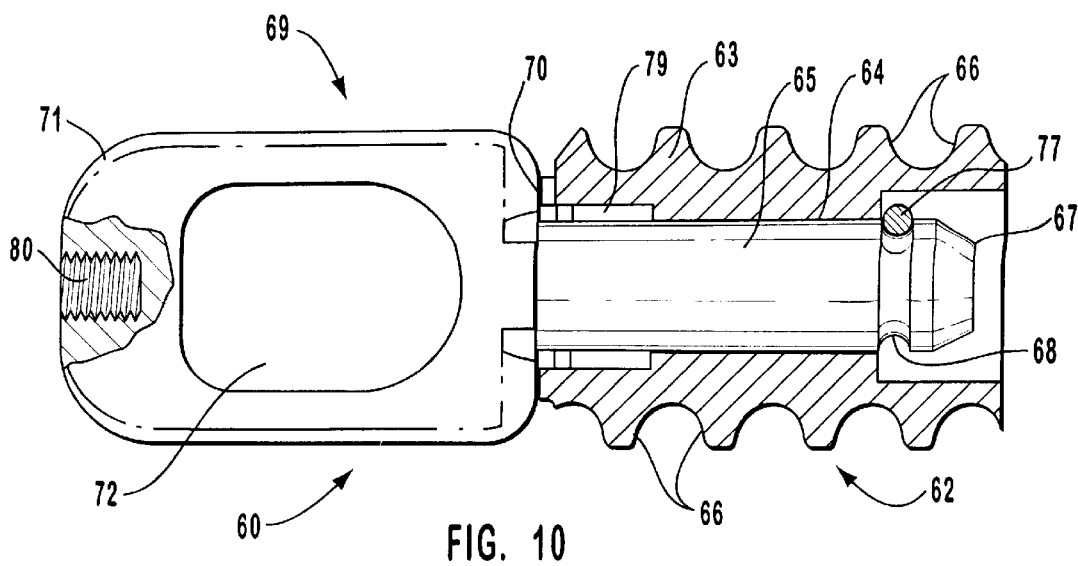
FIG. 10 is a side elevation view of the male and female members of FIGS. 8 and 9 coupled together.

FIGS. 7A through 7C show the threaded footing 62 taken from a forward or proximal end 75, with, in FIG. 7A, the tapered forward end 67 of the male member proximal portion 65 is shown as having passed through the distal portion of the threaded footing longitudinal passage 64 and with that tapered forward end 67 just engaging a coupling wire 77 that is mounted at its end 77a into a side of the longitudinal passage proximate to the proximal end 77 to extend across that passage. FIG. 7B shows the forward end 67 of the male member proximal portion 65 as having been further passed through the longitudinal passage 64 to where a taper thereof has engaged the coupling wire 77, deflecting it towards the wall of the longitudinal passage 64. FIG. 7C shows the male member tapered forward end 67 as having passed across the coupling wire 77 that has aligned with and has flexed into the male member proximal end groove 68, locking the male member 61 in the threaded flooring 62, as shown in FIGS. 6B and 10.

Shown in FIGS. 6A, 9 and 10, the threaded footing includes a rear or distal cavity 79 formed therein that is sided, for example, the wall surface is formed to have six equal sides, and is for receiving a turning tool, as illustrated and discussed hereinbelow with respect to FIG. 14 for use in turning as, for example, as shown in FIGS. 14, utilizing a base inserter tool 100, to seat the threaded footing 62 in a prepared bone tunnel end. Further, for guiding the male member 61 in a seated threaded footing 62, a tapped hole 80, as shown in FIGS. 6A, 6B, 8, 10 and 15, is formed as a longitudinal cavity in the center of the round rear or distal end 71 of the male member. Tapped hole 80 is for receiving a threaded proximal end of an insertion tool 105, shown in FIG. 16, that is maintained or held by an operator surgeon 108 who guides the male member 61 through a tibial end 84 of a tibial tunnel section 87, into a femoral tunnel section 88, to fit the male member proximal section 65 into the threaded footing 62 that has been turned into a tapped end of the femoral tunnel section 88 closed proximal end, as shown in FIG. 17.

Figure 11:
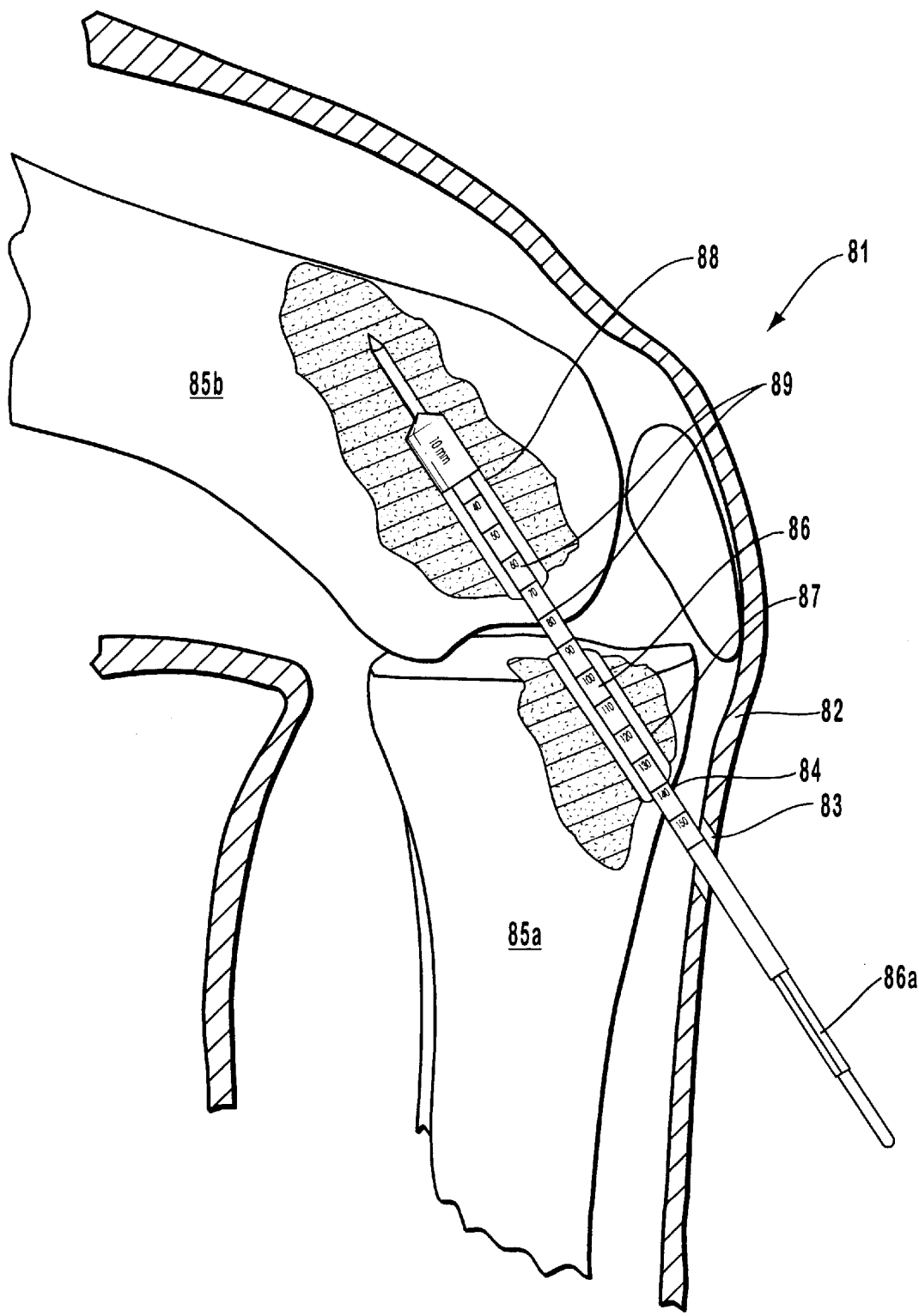
FIG. 11 is a side elevation sectional view showing a patient's knee, bent to approximately a ninety (90) degree angle, whereacross a straight tunnel is shown being drilled from a point on the tibial tuberosity, through an anterior cruciate ligament points of origin and into the distal femur utilizing a cannulated spade drill, forming a straight tunnel to a required diameter.

For installing a ligament graft as a replacement for an anterior cruciate ligament in a patient's knee 81, as shown in FIG. 11, with the knee bent appropriately, an incision 83 is formed through the skin 82 opposite to a drilling location 84 on the tibia 85a tuberosity. A surgeon operator then turns a cannulated space drill 86 as by fitting and turning end 86a in a chuck of a conventional drill, not shown, to form, in the tibia 85a and femur 85b, straight tunnel sections 87 and 88, respectively, to a required tunnel diameter. In which tuning, the surgeon operator can measure dept of drilling from the tibial tunnel end 84 by comparing the edge of that tunnel end with spaced markings 89 as are scribed, at spaced intervals along the cannulated drill to provide a straight tunnel of a desired length.

Shown in FIG. 12, the cannulated spade drill of FIG. 11 has been replaced with a stepped spade drill 90 that has an inwardly stepped drilling end 91 and, like the drill of FIG. 11, includes spaced markings 92 scribed at equal intervals therealong for use in measuring the total tunnel length to a blind or closed femoral tunnel end wherein the threaded footing 62 will be seated, as discussed hereinbelow.

FIG. 13 shows the stepped spade drill 90 of FIG. 12 as having been replaced with a tap 95. The tap 95 is used to tap so as to form threads in the stepped femoral tunnel end 93 and includes a straight shaft 96 with a tap 97 secured to its proximal end. The tap 97 is for fitting into femoral tunnel end to cut, when turned, threads therein to accommodate and mesh with the threads 66 of the threaded footing 62. A grip handle 98 is provided on the distal end of the straight shaft 96, extending axially therefrom, for gripping and turning by a surgeon operator to tap the femoral tunnel end 93.

FIG. 14 shows the tap 95 as having been removed from the tibial and femoral tunnel sections 87 and 88 and replaced with a threaded footing interter tool 100 that includes a straight shaft 101 having a threaded footing mount 102 on its top or proximal end, with handle 103 secured across its lower or distal end for turning by an operator surgeon. Like the spade drills described above, the straight shaft 101 preferably includes spaced marking 104 scribed at equal intervals therealong indicative of increments of distance that are for use in determining the distance the seated threaded footing 62 distal end is from the tibial tunnel end 84 for determining a length of ligament graft to be installed, as set out below.

Figure 8:
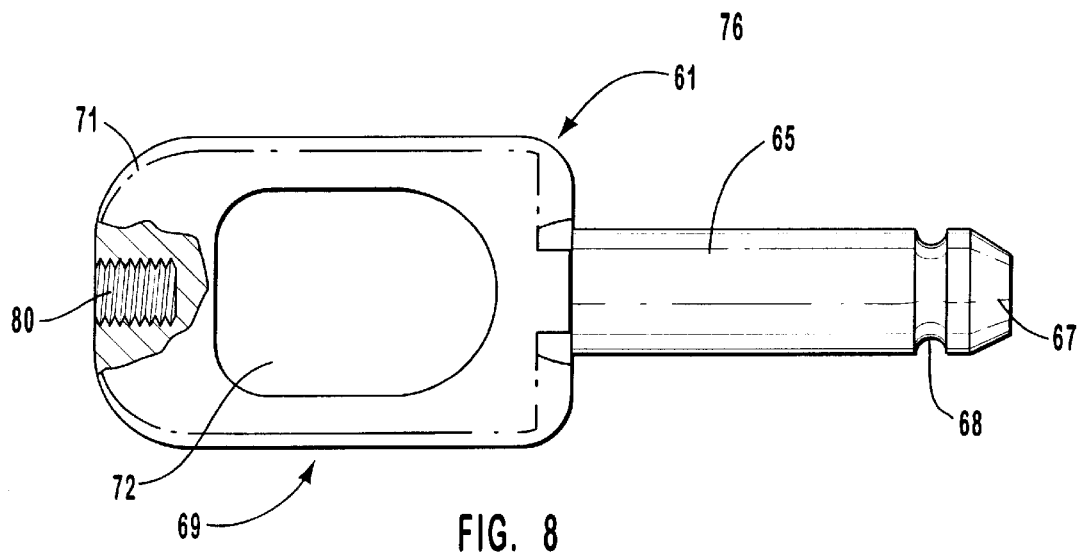
FIG. 8 is an enlarged side elevation view of the male member of FIG. 6A.
Figure 9:
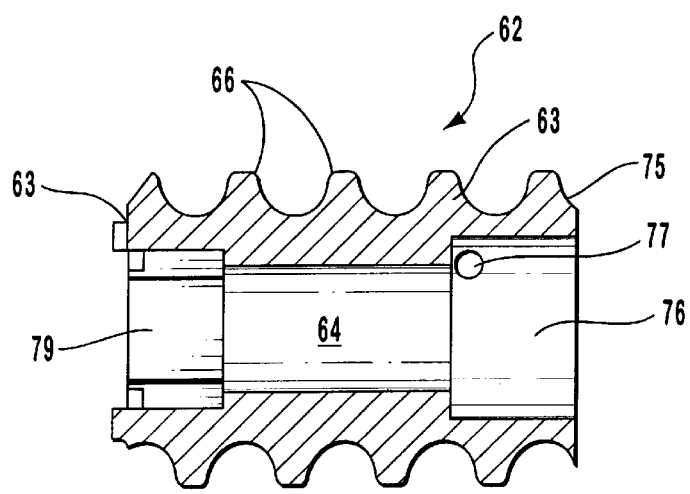
FIG. 9 is an enlarged side elevation sectional view of the female member threaded footing taken along the line 9—9 of FIG. 6A.

FIG. 15 shows a perspective view of the male member 61 of FIG. 8 with the ligament graft 73 shown threaded or fitted through the eyelet opening 72 before attachment to the insertion tool 105, as shown in FIG. 16. FIG. 16 shows the insertion tool 105 as including a straight shaft 106 with a threaded proximal end that has been turned into the male member 61 tapped hole 80, mounting the male member thereto. A surgeon operator's hand 108 is shown holding a tool cylindrical handle end 107, directing that male member 61 through the tibial tunnel section 87 and into the femoral tunnel section 88 to fit the end 67 of the male member proximal portion 65 into the threaded footing 62, as shown in FIG. 17.

FIG. 17 shows the male member 61 mounted in the threaded footing 62, as the bone fixator or ligament anchor system 60, with the ends of the ligament graft that has been fitted or threaded through the male member opening 72 and folded upon themselves and placed under tension, and mounted to the tibia cortex adjacent to the tibial tunnel end 84, utilizing a mounting clip 110. Which mounting clip 110 is shown as consisting of a plate 112 that is preferably somewhat curved across one face to conform to the tibia cortex surface whereto it is to be attached and includes legs or feet 111 that extend at approximately right angles downwardly from corners or edges of the curved face, the feet or leg 111 ends to pass into the tibia cortex. A center hole is formed in the plate 112 to pass a fastener 113 therethrough, such as a screw, that travels therethrough and into the tibia, pressing the ligament graft ends into to the tibia cortex surface, completing the ligament replacement procedure. As shown, the fastener 113, to provide for turning into the tibia, includes a recessed sided opening that is for receiving a turning tool, such as an Alan wrench, fitted therein, for turning the fastener 113 to where the installed fastener top surface is flush with the plate 112 surface.

While preferred embodiments of the present invention in a bone fixator or ligament anchor system and processes for their use have been shown and described herein, it should be apparent that the present disclosure is made by way of example only and that variations thereto are possible within the scope of the disclosure without departing from the subject matter coming with the scope of the following claims and a reasonable equivalency thereof, which claims we regard as our invention.

We claim:

1. A bone fixator for a ligament anchor system comprising, a footing means that includes a bone engaging outer surface for mounting in a bone tunnel and has a longitudinal passage therethrough that is stepped outwardly forming an interior shelf; a ligament carrying member means that includes a proximal portion, that is a straight cylindrical section having an inwardly slopping proximal end and includes a groove formed therearound back from said forward end; a coupling means is arranged in said longitudinal passage at said interior shelf for fitting in said proximal portion groove as a means for connection to said ligament carrying member when said proxinal portion of said ligament carrying member means is passed into said footing means to said interior shelf; a ligament graft mounting means arranged on said ligament carrying member means distal end for axially connecting said ligament graft thereto; and means for guiding an end of said ligament carrying member means proximal portion into said footing means longitudinal passage.

2. A bone fixator for a ligament anchor system as recited in claim 1, wherein the footing means is externally threaded along its length as the bone engaging surface; and the ligament carrying member means proximal portion has the groove formed across and adjacent to said inwardly sloped proximal end.

3. A bone fixator for a ligament anchor system as recited in claim 2, wherein a proximal end section of the footing means longitudinal passage interior shelf is at a right angle to the longitudinal axis of said longitudinal passage and includes, as the coupling means, a straight wire mounted at one end into said longitudinal passage wall to extend outwardly therefrom across said longitudinal passage and to fit into the ligament carrying member proximal portion groove that is a continuous groove encircling said ligament carrying member proximal portion.

4. A bone fixator for a ligament anchor system as recited in claim 2, wherein the footing means includes flat proximal and distal faces, and the longitudinal opening adjacent to at least one of said faces is walled for receiving an end of a driver shaft fitted therein as a means for turning said footing means into or out of a bone tunnel.

5. A bone fixator for a ligament anchor system as recited in claim 2, wherein the ligament carrying member means includes an eyelet means, formed as a distal portion thereof, to receive a ligament graft fitted therethrough, and the means for guiding said ligament carrying member means is a tapped hole formed axially into a distal end of said eyelet means that is to receive and releasable connect to an end of an insertion tool fitted and turned therein.

6. A bone fixator for a ligament anchor system as recited in claim 2, further including a longitudinal hole formed in the center of a proximal surface of the straight cylindrical section, which said longitudinal hole is arranged to receive and releasable connect to an end of an insertion tool means fitted therein for pulling said ligament carrying member means straight cylindrical section into the footing means.

7. A bone fixator for a ligament anchor system as recited in claim 1, wherein the footing means is formed from a biodegradable material.

8. A bone fixator for a ligament anchor system as recited in claim 1, wherein the footing means and the ligament carrying member are both formed from a biodegradable material.

9. A process for mounting a ligament graft in a bone tunnel in an arthroscopic surgical procedure comprising the steps of, forming a tunnel into a bone to a measured depth and, through an open tunnel end, passing a footing that includes a longitudinal opening formed therethrough and is releasably maintained to an end of an insertion tool for position said footing in a proximal end of said bone tunnel, and during said footing positioning, measuring the location of said footing from said open tunnel to a desired tunnel depth; axially connecting a ligament graft, that has a selected length as determined by the measured distance of said footing from said open tunnel end to a distal end of a ligament carrying member that includes a proximal portion having a proximal portion having a sloped proximal end and includes a groove formed thereacross said sloped proximal end for fitting into said footing longitudinal opening; providing a locked arrangement within said footing to engage said groove of said liagment carrying member proximal portion while allowing said proximal portion to travel into said footing and to lock into said groove; and, with the ligament graft under tension, securing the ligament graft distant from the liagment carrying member to a bone surface adjacent to the bone tunnel open end.

10. A process as recited in claim 9, wherein the footing is threaded along its outer surface and at least one end of the footing longitudinal opening is sided to receive a tool having a like sided end fitted therein for turning said threaded footing into the bone tunnel end; and at least one end section of said threaded footing longitudinal opening is stepped outwardly to provide a flat step wherein a straight section of wire is secured at one end to extend across said footing longitudinal opening stepped portion as the locking arrangement.

11. A process as recited in claim 9, wherein a distal portion of the ligament carrying member includes an eyelet section to receive a ligament graft fitted therethrough and folded upon itself.

12. A process as recited in claim 9, wherein a distal portion of the ligament carrying member includes a ligament mounting section that incorporates at least one pointed end post extending therefrom forming essentially a right angle to the ligament carrying member proximal portion, which said post is for skewering to mount an end of a ligament graft thereto, with said ligament graft to extend axially from said ligament carrying member.

13. A process as recited in claim 12, further including, to the ligament graft end, forming at least one transverse hole formed therein to conform to and to receive the pointed end post; and applying pressure to said ligament graft end to urge said pointed end post through said transverse hole, seating said ligament graft end the ligament carrying member ligament mounting section.

14. A process as recited in claim 13, wherein the ligament graft has at least one bone end wherethrough the transverse hole is formed.

15. A process as recited in claim 9, further including, after ligament graft tensioning and mounting, adjusting ligament tensioning by altering the positioning of the footing means in the bone tunnel, by appropriately turning it in the bone tunnel.

16. A process as recited in claim 15 wherein the footing means positioning in the bone tunnel is altered to adjusted ligament graft tension by turning said footing means in said bone tunnel.

* * * * *